(12) United States Patent
Takeuchi et al.

(10) Patent No.: US 7,850,599 B2
(45) Date of Patent: Dec. 14, 2010

(54) ENDOSCOPE APPARATUS

(75) Inventors: Shinji Takeuchi, Saitama (JP); Kazunori Abe, Saitama (JP); Daisuke Ayame, Saitama (JP); Mitsuru Higuchi, Saitama (JP)

(73) Assignee: Fujinon Corporation, Saitama (JP)

( * ) Notice: Subject to any disclaimer, the term of this patent is extended or adjusted under 35 U.S.C. 154(b) by 1196 days.

(21) Appl. No.: 11/365,861

(22) Filed: Mar. 2, 2006

(65) Prior Publication Data

US 2006/0211915 A1 Sep. 21, 2006

(30) Foreign Application Priority Data

Mar. 4, 2005 (JP) .......................... P.2005-060200
Oct. 14, 2005 (JP) .......................... P.2005-300191
Oct. 14, 2005 (JP) .......................... P.2005-300192

(51) Int. Cl.
*A61B 1/04* (2006.01)
(52) U.S. Cl. ..................................... 600/109
(58) Field of Classification Search ................. 600/101, 600/109, 118; 348/65, 70, 76
See application file for complete search history.

(56) References Cited

U.S. PATENT DOCUMENTS

| 4,885,634 | A | 12/1989 | Yabe |
| 4,914,512 | A | 4/1990 | Sekiguchi |
| 5,331,551 | A * | 7/1994 | Tsuruoka et al. ............ 382/128 |
| 5,408,263 | A * | 4/1995 | Kikuchi et al. ............... 348/68 |
| 5,675,378 | A | 10/1997 | Takasugi et al. |
| 7,204,803 | B2 * | 4/2007 | Ueno et al. .................. 600/109 |
| 2001/0033364 | A1 * | 10/2001 | Cabib et al. ................. 351/221 |
| 2002/0177751 | A1 * | 11/2002 | Ueno et al. .................. 600/160 |
| 2004/0046865 | A1 * | 3/2004 | Ueno et al. ................... 348/70 |

FOREIGN PATENT DOCUMENTS

| EP | 1302152 A | 4/2003 |
| EP | 1491132 A | 12/2004 |
| JP | 9-120033 A | 5/1997 |
| JP | 2002-34908 A | 2/2002 |
| JP | 2003-93336 | 4/2003 |

OTHER PUBLICATIONS

"Analysis and Evaluation of Digital Color Images" University of Tokyo Press, 2000, pp. 148-153.

* cited by examiner

*Primary Examiner*—Philip R Smith
(74) *Attorney, Agent, or Firm*—Birch, Stewart, Kolasch & Birch, LLP

(57) ABSTRACT

An endoscope apparatus comprises: an endoscope comprising an imaging device that forms a color image signal of a body to be observed; a storage portion that stores matrix data regarding a wavelength range in which a spectral image is constituted; a spectral image forming circuit that conducts matrix calculation based on the color image signals by using the matrix data of the storage portion and forms a spectral image of a selected wavelength range; and a wavelength selecting section that selects the wavelength range of the spectral image formed by the spectral image forming circuit through a continuous changeover or a step-wise changeover.

18 Claims, 9 Drawing Sheets

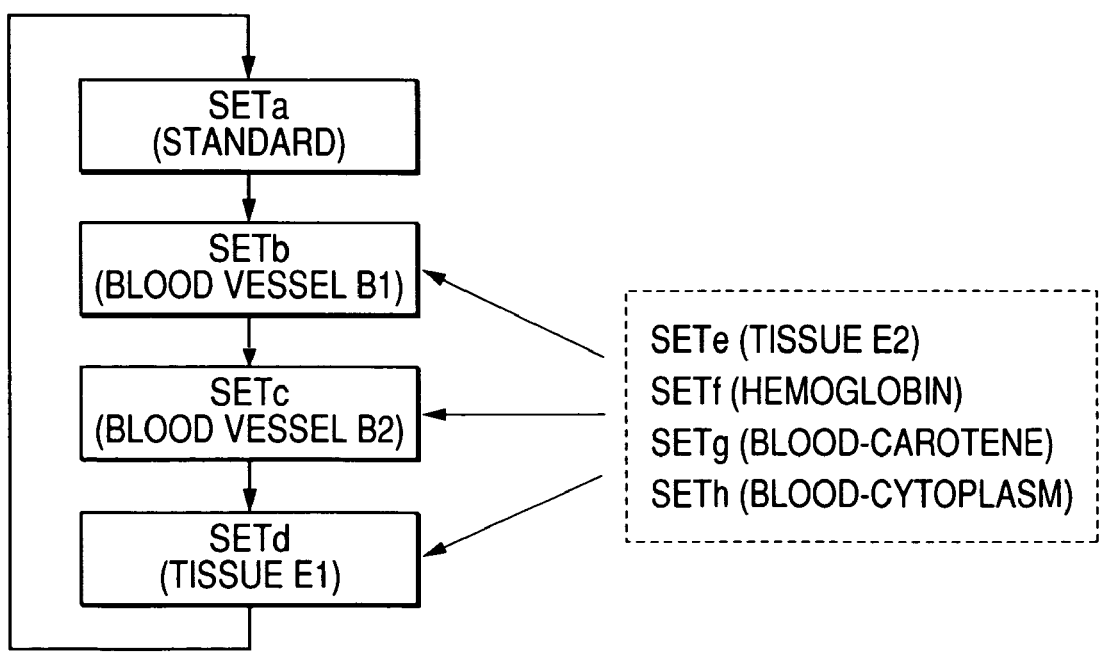

ENDOSCOPE APPARATUS

This Nonprovisional application claims priority under 35 U.S.C. §119(a) on Patent Application No(s). JP 2005-060200, JP 2005-300191, JP 2005-300192 filed in Japan on Mar. 4, 2005, Oct. 14, 2005, and October 2005, respectively, the entire contents of which are hereby incorporated by reference.

BACKGROUND OF THE INVENTION

1. Field of the Invention

The present invention relates to an endoscope apparatus, more particularly, a constitution used in medical fields for forming and displaying a spectral image (video) made up of image information of arbitrarily selected wavelength ranges.

2. Description of the Related Art

Recently, in an electronic endoscope apparatus which uses a solid imaging device, spectral imaging combined with a narrow band pass filter on the basis of a spectral reflectance in alimentary canal (gastric mucosa and the like), namely, a narrow band filter built-in an electronic endoscope apparatus (Narrow Band Imaging—NBI) has become the focus of attention. In place of rotational filters of R (red), G (green) and B (blue) by a frame sequential method, this system is provided with band pass filters of three narrow bands (wavelengths), outputs sequentially illumination light via these narrow band pass filters, and conducts processing the same as in the case of red (R), green (G) and blue (B) signals while changing respective weightings to three signals obtained from these illumination lights, thereby forming a spectral image. This spectral image is able to realize micro-structures and the like in gastrointestinal tracts such as the stomach and large intestine, which would otherwise not be realized.

In contrast, unlike the frame sequential method using the above-described narrow band pass filters, as described in Japanese Published Unexamined Patent Application No. 2003-93336, and Yoichi Miyake "Analysis and Evaluation of Digital Color Images," University of Tokyo Press, 2000, pp. 148-153, it has been proposed that in the simultaneous method in which micro-mosaic color filters are arranged on a solid imaging device, a spectral image is formed by the computing process on the basis of image signals obtained from white light. In this method, the relationship between numeric data of the respective R, G, and B color sensitivity characteristics and numeric data of spectral characteristics of a specific narrow band pass is determined as matrix data (coefficient sets) and computing is made for the matrix data and the R, G and B signals to obtain spectral image signals artificially via the narrow band pass filters. Where a spectral image is formed by such computing, it is not necessary to provide a plurality of filters corresponding to desired wavelength ranges and to provide these change-over arrangements, thereby successfully avoiding increases in the size of a system and reducing cost.

However, in forming a spectral image in the above-described endoscope apparatus, areas of interest to be visualized are in a plurality of types and conditions such as relatively thick blood vessels, capillary vessels, deep-positioned vessels, shallow-positioned vessels, cancerous tissues different in progression, and the relationship between the targets and the wavelength ranges to be selected may vary depending on the individual differences in areas of interest to be observed, therefore, it is difficult to select and establish a wavelength range for obtaining an optimal spectral image in which an expected target is visualized.

On the other hand, a wavelength range where a difference between specific substances is visualized as a target, for example, a difference between oxyhemoglobin and deoxyhemoglobin, has been clarified, and it is preferable that a spectral image set at a predetermined wavelength range can promptly be obtained.

Further, since the most appropriate wavelength ranges in forming and displaying the spectral image easy to be clinically observed are often different among the operators of the apparatus such as clinical doctors, if the wavelength ranges thought to be optimum are previously prepared in accordance with the regions of the objects, each of the clinical doctors cannot utilize them in forming spectral images, and in some cases, he or she needs to perform the operation of selecting the wavelength ranges suited to his or her feeling by the minute. Accordingly, it takes much time for each operator of the apparatus to form and display the spectral image easiest for the operator to observe.

The invention has been reached in view of the problem described above, and has an object of providing an endoscope apparatus with which each of the operators of the apparatus can quickly form and display a spectral image easiest for the operator to observe.

SUMMARY OF THE INVENTION

The present invention has been made in view of the above problems, an object of the invention is to provide an endoscope apparatus capable of instantly and easily selecting a wavelength range for forming the spectral image in which a desired target has been visualized.

In order to attain the above object, an endoscope apparatus according to a first aspect of the invention comprises: an endoscope comprising an imaging device that forms a color image signal of a body to be observed; a storage portion that stores matrix data (coefficient data) regarding a wavelength range in which a spectral image is constituted; a spectral image forming circuit that conducts matrix calculation based on the color image signals by using the matrix data of the storage portion and forms a spectral image of a selected wavelength range; and a wavelength selecting section that selects the wavelength range of the spectral image formed by the spectral image forming circuit through a continuous changeover or a step-wise changeover.

An endoscope apparatus according to a second aspect of the invention comprises a wavelength changeover width setting section for variably setting a changeover width of the wavelength range to be selected by the wavelength selecting section.

An endoscope apparatus according to a third aspect of the invention comprises:

an endoscope comprising an imaging device that forms a color image signals of a body to be observed;

a storage portion that stores matrix data regarding a set of wavelength ranges in which a spectral image is constituted;

a spectral image forming circuit that conducts matrix calculation based on the color image signals by using the matrix data of the storage portion and forms a spectral image of a selected set of wavelength ranges; and a wavelength selecting section that sets a plurality of sets of wavelength ranges (matrix data), each of the sets of wavelength ranges being for the spectral image formed by the spectral image forming circuit, and selects one of the sets of wavelength ranges by changing the sets of wavelength ranges.

According to a fourth aspect of the invention, there is provided the endoscope apparatus wherein the wavelength selecting section is able to select a set of wavelength ranges having the same range (single wavelength range) for formation of a spectral image by a single color mode, from the sets of wavelength ranges.

According to a fifth aspect of the invention, there is provided the endoscope apparatus wherein the wavelength sets which can be selected by the wavelength selecting section comprise: a wavelength set for visualizing a difference between oxyhemoglobin and deoxyhemoglobin; a wavelength set for visualizing a difference between blood and carotene; and a wavelength set for visualizing a difference between blood and cytoplasm.

In the above-described constitution, in order to obtain $\lambda 1$, $\lambda 2$ and $\lambda 3$ signals of wavelength narrow bands (components) by matrix calculation from RGB signals, matrix data made up of 61 wavelength-range parameters (coefficient sets, p1 to p61) in which a wavelength range from 400 nm to 700 nm, for example, is divided at 5 nm intervals are stored in the computing memory of a processor unit. Then, when an operator uses the wavelength selecting section to select three wavelength ranges (one wavelength range may be acceptable), the matrix data corresponding to these three wavelength ranges are read from the memory. In the spectral image forming circuit, $\lambda 1$, $\lambda 2$ and $\lambda 3$ signals are formed from the RGB signals output from the matrix data, DSP and the like, and these $\lambda 1$, $\lambda 2$ and $\lambda 3$ signals form a spectral image.

In the wavelength selecting section, individual switches and the keyboard of an operation panel provided on the processor unit can be operated to select wavelength ranges of the $\lambda 1$, $\lambda 2$ and $\lambda 3$ by changing at a 1 nm width continuously or by a stepwise way at a width such as 5 nm, 10 nm or 20 nm stepwise. Then, the changeover width can be selected by a changeover width setting switch.

Further, in constitutions described in the third to fifth aspects of the invention, the wavelength selecting section, namely a switch and like, is used to select a wavelength set for visualizing blood vessels, that for visualizing specific tissues such as cancerous tissues and that for visualizing a difference between oxyhemoglobin and deoxyhemoglobin and difference between blood and carotene, or a difference between blood and cytoplasm, thereby making it possible to form easily a spectral image for a specific target.

With the above-mentioned endoscope apparatus of the present invention, a wavelength range can be selected at any given set changeover width, and a predetermined wavelength set is selected, thereby making it possible to select easily and promptly a wavelength range for a spectral image in which a desired target is visualized and also to provide information helpful in making a diagnosis by displaying on a monitor and the like a spectral image in which a difference between a blood vessel and specific tissue or that between oxyhemoglobin and deoxyhemoglobin is visualized.

According to a sixth aspect of the invention, there is provided the endoscope apparatus in the first aspect of the invention, further comprising a wavelength storing section that stores the wavelength range selected by the wavelength selecting section.

According to a seventh aspect of the invention, there is provided the endoscope apparatus in the third aspect of the invention, further comprising a wavelength storing section that stores the set of wavelength ranges selected by the wavelength selecting section.

Note that the wavelength storing section of the endoscope apparatus according to the sixth or seventh aspect of the invention preferably comprises, in addition to an area that stores the (set of) wavelength range(s), a default data storing area that stores a (set of) initial setting value(s) (default value (s)) for the (set of) wavelength range(s) selected by the wavelength selecting section.

Further, the wavelength storing section preferably comprises, in addition to the area that stores the (set of) wavelength range(s), a changed wavelength storing area that stores a wavelength range changed after read out from the area that stores the (set of) wavelength range(s). In this case, the endoscope apparatus according to the sixth or the seventh aspect of the invention preferably comprises a configuration of storing the wavelength range (s) stored in the changed wavelength storing area to the area that stores the (set of) wavelength range(s).

According to the above-mentioned endoscope apparatus of the invention, by providing the wavelength storing section for storing the wavelength range selected by the wavelength selecting section or a plurality of wavelength ranges as the wavelength set, it becomes possible for the operator of the apparatus such as a clinical doctor to store to the wavelength storing section the wavelength range considered to be the best suited to him or her and once selected. In such a case, when the operator of the apparatus forms and displays the spectral image next time or later, he or she can retrieve the stored wavelength range to use it again, thus the spectral image easiest for the user to observe can quickly be formed and then displayed.

Further, in particular, in the case in which the wavelength storing section of the endoscope apparatus according to the invention further includes, in addition to the area that stores the wavelength range(s), a default data storing area that stores initial setting value(s) of the wavelength range(s) selected by the wavelength selecting section, the initial setting values can be read out therefrom to be utilized. In such a case, the confusion in judging the most suitable wavelength ranges caused by repeated reselection of the wavelength range can be cleared up by reset the wavelength range with the initial setting value forming a reference Further, in the case in which the wavelength storing section further includes, in addition to the area for storing the wavelength range(s), a changed wavelength storing area that stores wavelength range(s) changed after read out from the area that stores the wavelength range(s), the operation of changing the wavelength range can be conducted utilizing the changed wavelength storing area, thus such a problem as overwriting the wavelength range stored in the area for storing the wavelength range(s) with a wrong value can be prevented.

In addition, the invention has an object of providing an electronic endoscope apparatus capable of offering easier operation of switching between an ordinary image and a desired diagnostic image.

According to an eighth aspect of the invention, there is provided the electronic endoscope apparatus which is capable of displaying alternatively by switching an ordinary image of a biological mucous membrane and a diagnostic image of the biological mucous membrane, the diagnostic image being obtained by matrix calculation (spectral image estimation calculation) based on the selected one of said plurality sets of wavelength ranges, the electronic endoscope apparatus comprising a latest wavelength set storing section that stores the most recently selected one of the sets of wavelength ranges as a latest wavelength set, wherein the diagnostic image corresponding to the latest wavelength set stored in the latest wavelength set storing section is displayed in response to switching from the ordinary image to the diagnostic image.

The latest wavelength set storing section can include a backup section that enables the latest wavelength set storing section to keep storing the latest wavelength set even when a drive power of the electronic endoscope apparatus is in an OFF state.

Note that the storing section is not limited to one storing the wavelength set itself, but can be one storing something substantially suggesting the wavelength set.

The inventors have reached the knowledge that the diagnostic image displayed right before switching to an ordinary image is often displayed in switching back from the ordinary image to the diagnostic image while making a diagnosis of a biological mucous membrane using an electronic endoscope apparatus capable of displaying alternatively an ordinary image and plural kinds of diagnostic images composed of the narrow-band spectral images, and have reached the invention based on the knowledge. In other words, the invention is reached based on a knowledge that a specific wavelength set suitable for diagnosis of a biological mucous membrane is once determined, switching of display between the ordinary image and the diagnostic image corresponding to the specific wavelength set is often executed repeatedly in the electronic endoscope apparatus described above.

The electronic endoscope apparatus according to the invention is equipped with a latest wavelength set storing section for storing the most recently selected one of the wavelength sets, and is configured to display the diagnostic image corresponding to the latest wavelength set stored in the latest wavelength set storing section in response to switching from the ordinary image to the diagnostic image, thus the switching operation between the ordinary image and the desired diagnostic image can more easily be executed.

Namely, in general, it is highly probable that the diagnostic image expected to be displayed when switching back from the ordinary image to the diagnostic image is the diagnostic image displayed right before the ordinary image is displayed. In such a case, the desired diagnostic image can be realized by displaying the diagnostic image corresponding to the wavelength set stored in the storing section, thus the switching operation from the ordinary image to the desired diagnostic image can more easily be executed.

Further, if the latest wavelength set storing section is provided with a backup section for enabling the latest wavelength set storing section to keep storing the wavelength set even when a drive power of the electronic endoscope apparatus is in an OFF state, the operation of displaying the desired diagnostic image can more surely be executed.

BRIEF DESCRIPTION OF THE DRAWINGS

FIG. 7 is a chart showing wavelength sets selected in the single color mode in the endoscope apparatus shown in FIG. 1;

FIG. 8 is a flowchart which explains another example of the changeover of the wavelength set by the set changeover switch of the embodiment;

DETAILED DESCRIPTION OF THE INVENTION

Figure 1:
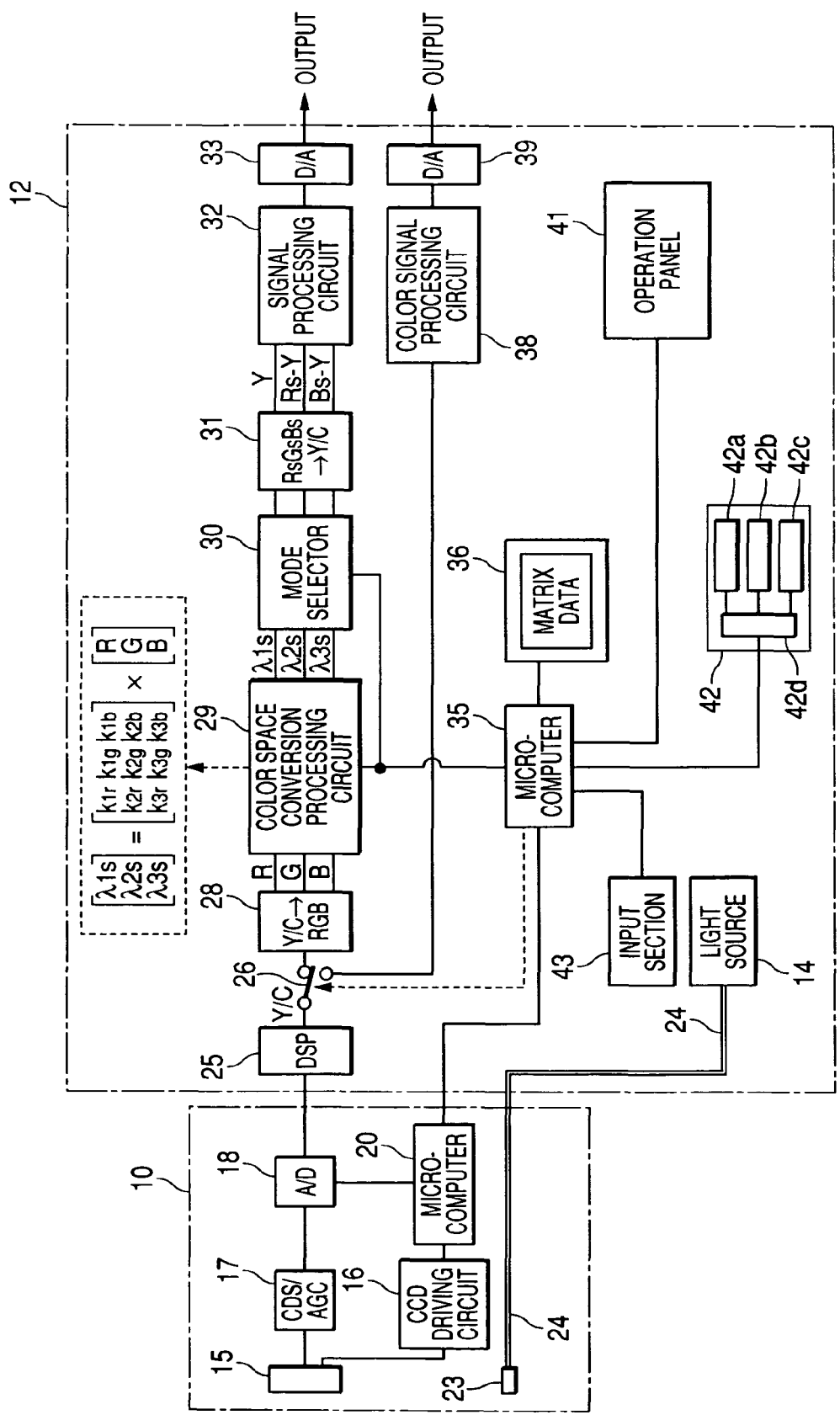
FIG. 1 is a block diagram showing a configuration of an endoscope apparatus according to an embodiment of the invention.

FIG. 1 shows a constitution of the electronic endoscope apparatus according to an embodiment in the present invention. As shown in the figure, the electronic endoscope apparatus is constituted in such a manner that a scope (electronic endoscope) 10, namely a main body section of the endoscope apparatus, is connected to a processor unit 12 in a freely attachable and detachable way and a light source 14 emitting for example white light is arranged in the processor unit 12. Further, there is a case where the light source 14 may be arranged on a light source unit, which is a separate body. The scope 10 is provided on the end with a CCD 15 which is a solid imaging device, and the CCD 15 includes, for example, a complementary color-type CCD having color filters of Mg (magenta), Ye (yellow), Cy (cyan) and G (green) and an elementary color-type CCD having R, G and B color filters on an imaging surface.

The CCD 15 is provided with a CCD driving circuit 16 for forming a driving pulse on the basis of synchronizing signals, a CDS/AGC (correlated dual sampling/automatic gain control) circuit 17 for sampling and amplifying an image (video) signal input from the CCD 15 the image signal and an A/D converter 18. Also arranged is a microcomputer 20 for controlling various circuits inside the scope 10 and also controlling communications with the processor unit 12. Further, the scope 10 is provided at the end with an illumination window 23, which is connected to the light source 14 by a light guide 24.

The processor unit 12 is provided with a DSP (digital signal processor) 25 which imparts a variety of image processings to digitally converted image signals. In the DSP 25, Y/C signals constituted by a brightness (Y) signal and a color difference [C(R−Y, B−Y)] signal are formed and output from the output signal of the above-mentioned CCD 15. In the embodiment, it is possible to form and display selectively ordinary images (moving image and still image) and spectral images (moving image and still image). The DSP 25 is provided (at the other end) with a first color conversion circuit 28 via a selector 26 for selecting formation of an ordinary image or that of a spectral image. In the first color conversion circuit 28, the Y (brightness)/C (color difference) signals output from the DSP 25 are converted to RGB signals. Further, the DSP 25 may be arranged on the scope 10.

At the post stage of the first color conversion circuit 28, a color space conversion processing circuit 29 (corresponding to the spectral image forming circuit) for conducting matrix calculation for spectral images and outputting spectral image signals of the selected wavelength $\lambda 1$, $\lambda 2$ or $\lambda 3$, a mode selector 30 for selecting either spectral images made up of one wavelength range (narrow band) (single color mode) or spectral images made up of three wavelength ranges (3-color mode) (the mode selector may be provided with a two-color mode for selecting two colors), a second color conversion circuit 31 for inputting image signals (λ1s, λ2s and λ3s) in one wavelength range or in three wavelength ranges as Rs, Gs and Bs signals in order to make a processing which corresponds to conventional RGB signals and converting Rs, Gs and Bs signals to Y/C signals and a signal processing circuit 32 for conducting a variety of other signal processings (mirror image process, mask generation, character generation and the like), and D/A converter 33.

Further, a microcomputer 35 is provided inside the processor unit 12 shown in FIG. 1, which makes communications with the scope 10, controls respective circuits inside the processor unit 12 and reads matrix data from a memory 36 (corresponding to the storage memory) to provide them with the color space conversion processing circuit 29. The memory 36 stores matrix (coefficient) data (table) for forming a spectral image on the basis of RGB signals. The following Table 1 shows one example of the matrix data which is accommodated into the memory 36 of the embodiment in the present invention.

TABLE 1

| Parameter | $k_{pr}$ | $k_{pg}$ | $k_{pb}$ |
|---|---|---|---|
| p1 | 0.000083 | −0.00188 | 0.003592 |
| . | . | . | . |
| . | . | . | . |
| . | . | . | . |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| . | . | . | . |
| . | . | . | . |
| . | . | . | . |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −0.000036 |
| p51 | 0.005152 | −0.00192 | 0.000088 |
| p52 | 0.005215 | −0.00207 | 0.000217 |
| . | . | . | . |
| . | . | . | . |
| . | . | . | . |
| p61 | 0.00548 | −0.00229 | 0.00453 |

The matrix data shown in the above Table 1 includes, for example, 61 wavelength-range parameters (coefficient sets) p1 to P61 in which a wavelength range of 400 nm to 700 nm is divided at 5 nm intervals. The parameters p1 to p61 are constituted by coefficients, $k_{pr}$, $k_{pg}$ and $k_{pb}$ (p corresponds to p1 to p61) for matrix calculation.

Then, in the color space conversion processing circuit 29, matrix calculation is carried out according to the following mathematical formula 1 by referring to the above coefficients, $k_{pr}$, $k_{pg}$ and $k_{pb}$, and RGB signals output from the first color conversion circuit 28 to form the spectral image signals λ1s, λ2s, and λ3s.

$$\begin{bmatrix} \lambda 1 \\ \lambda 2 \\ \lambda 3 \end{bmatrix} = \begin{bmatrix} k_{1r} & k_{1g} & k_{1b} \\ k_{2r} & k_{2g} & k_{1b} \\ k_{3r} & k_{3g} & k_{3b} \end{bmatrix} \times \begin{bmatrix} R \\ G \\ B \end{bmatrix} \quad \text{[Mathematical Formula 1]}$$

Namely, in the case in which the wavelength ranges λ1, λ2, and λ3 of, for example, 500 nm, 620 nm, and 650 nm are selected as those forming the spectral image, the coefficients (−0.00119, 0.002346, 0.0016) of a parameter p21 corresponding to the center wavelength of 500 nm, the coefficients (0.004022, 0.000068, −0.00097) of a parameter p45 corresponding to the center wavelength of 620 nm, and the coefficients (0.005152, −0.00192, 0.000088) of a parameter p51 corresponding to the center wavelength of 650 nm out of 61 sets of parameters are used as the coefficients ($k_{pr}$, $k_{pg}$, and $k_{pb}$) in the formula to execute the operation. Note that such parameters are read out from a memory 36 based on combinations of the wavelengths stored in a wavelength set memory 42 described below as described later.

Further, a color signal processing circuit 38 for forming an ordinary color image, not the spectral image, is connected to the other output terminal of the selector 26, and a D/A converter 39 is connected to the color signal processing circuit 38.

Figure 2:
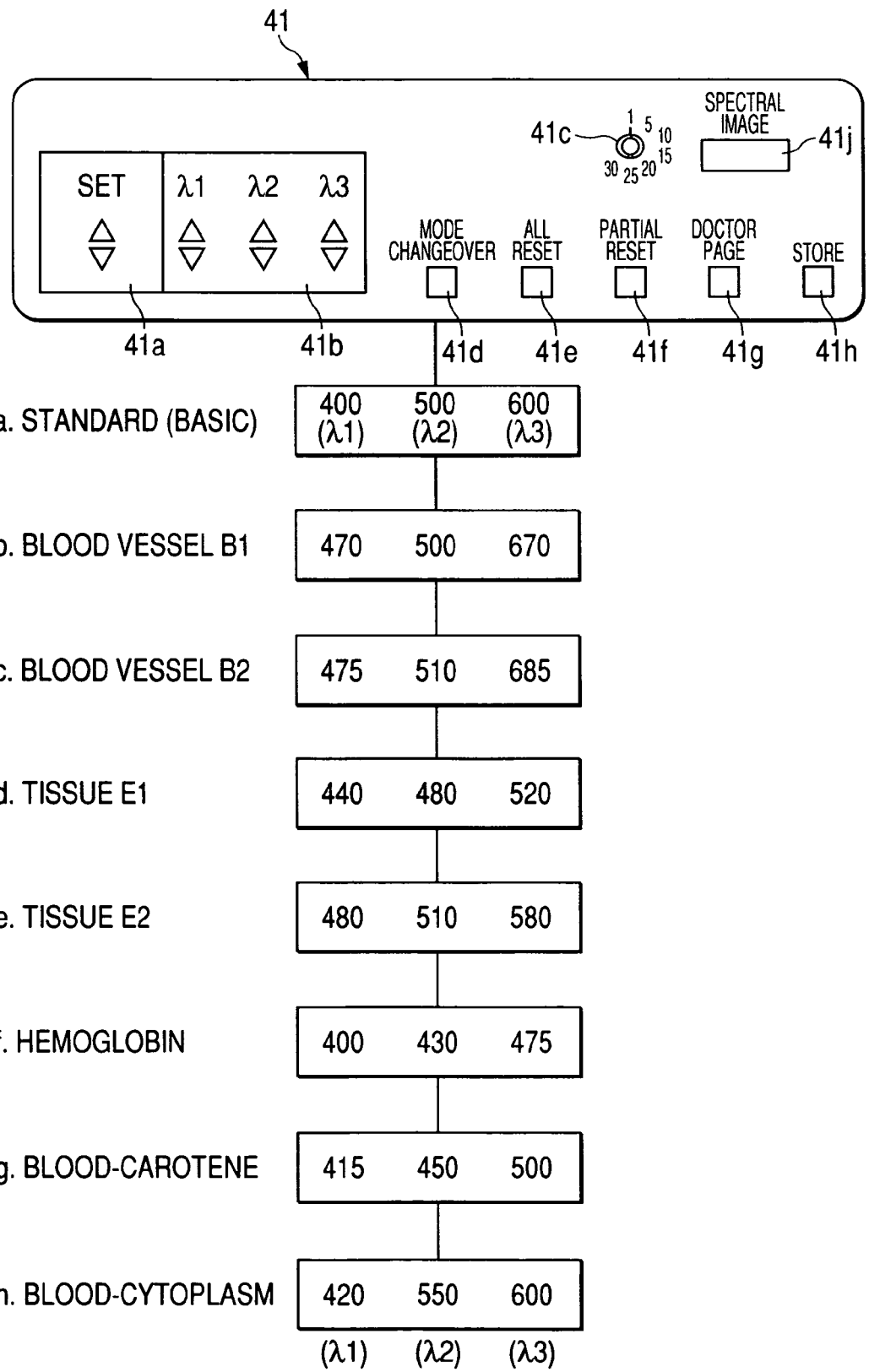
FIG. 2 is a diagram showing a configuration of an operation panel of a processor unit forming the endoscope apparatus shown in FIG. 1 and an example of wavelength sets.

In addition to the memory 36, an operation panel 41, the wavelength memory 42, and an input section 43 composed of a keyboard and so on are connected to the microcomputer 35. FIG. 2 shows the operation panel 41 in detail. The operation panel 41 is equipped with a set selecting switch 41a for selecting one of the wavelength sets a through h, for example, schematically shown integrally in FIG. 2, a wavelength selection switch 41b for selecting the center wavelength of each of the wavelength ranges λ1, λ2, and λ3, a changeover width setting switch 41c for setting the amount of change in the wavelength executed with the wavelength selection switch 41b, a mode changeover switch 41d for switching the mode between a single color mode and a three color mode, an all reset switch 41e for resetting all the wavelength ranges in all of the wavelength sets a through h with the initial values described below, a partial reset switch 41f for resetting the wavelength ranges of either one of the wavelength sets a through h with the initial values, a doctor page switch 41g for writing the wavelength sets a through h prepared for each of the operators of the apparatus such as clinical doctors into the wavelength set memory 42 and retrieve them therefrom, a storing switch 41h for storing the wavelength sets to the wavelength set memory 42, and spectral image forming switch 41j for instructing formation of the spectral image. Note that the spectral image forming switch 41j can be provided to the scope 10 side.

The wavelength selecting switch 41b is able to select a center wavelength, irrespective of the wavelength range of the wavelength set set on the set selecting switch 41a and also able to change and select a wavelength range by referring to a value of the wavelength set selected by the set selecting switch 41a as a starting position. Then, the microcomputer 35 supplies to the color space conversion processing circuit 29 matrix data of the wavelength range λ1, λ2 or λ3 selected by the signal of the switches 41a through 41e. Further, the functions of these switches may be allocated to keys on the keyboard.

The operation of the electronic endoscope apparatus according to the present embodiment having the configuration described above will hereinafter be explained. Firstly, formation of the ordinary image and the spectral image is explained. As shown in FIG. 1, in the scope 10, the CCD 15 driven by the CCD driving circuit 16 takes the mage of the object of observation to output an image pickup signal. The image pickup signal goes through the correlative double sampling process and is amplified with the operation of the automatic gain control in the CDS/AGC circuit 17, A/D-converted in the A/D converter 18, and then inputted in the DSP 25 of the processor unit 12 as a digital signal.

In the DSP 25, the gamma process is executed on the output signal from the scope 10, and at the same time, the color conversion process is executed on the signals obtained through the color filters of Mg, Ye, Cy, and G to form the Y/C signal composed of the luminance (Y) signal and the color-difference (R−Y, B−Y) signals. The output of the DSP 25 is normally supplied to the color signal processing circuit 38 by the selector 26, and goes through predetermined processes such as a mirror image process, a mask generation process, a character generation process and so on in this circuit 38, and is then supplied to the monitor 34 shown in FIG. 3 after converted into an analog signal by the D/A converter 39. Thus, the ordinary color image of the observation object can be displayed on the monitor 34.

Meanwhile, if the spectral image forming switch 41j of the operation panel 41 shown in FIG. 2 is operated, the selector 26 is switched to be the state for supplying the first color converting circuit 28 with the Y/C signal outputted from the DSP 25, and the Y/C signal is then converted into the RGB signal by this circuit 28. The RGB signal is then supplied to the color space conversion processing circuit 29, and in the color space conversion processing circuit 29, the matrix operation according to Formula 1 described above for forming the spectral image is executed with the RGB signal and the matrix data. Namely, in the process of forming the spectral image, the three wavelength ranges $\lambda 1$, $\lambda 2$, and $\lambda 3$ are set by operating the operation panel 41 described later, and the microcomputer 35 reads out the matrix data corresponding to those three selected wavelength ranges from the memory 36, and then inputs them to the color space conversion processing circuit 29.

For example, the three wavelength ranges $\lambda 1$, $\lambda 2$, and $\lambda 3$ of 500 nm in wavelength, 620 nm, and 650 nm, respectively, are selected, the coefficients of the parameters p21, p45, and p51 in Table 1 respectively corresponding to the wavelength ranges are used for forming the spectral image signals $\lambda 1s$, $\lambda 2s$, and $\lambda 3s$ from the RGB signal by the matrix operation of mathematical formula 2.

$$\begin{bmatrix} \lambda 1 \\ \lambda 2 \\ \lambda 3 \end{bmatrix} \begin{bmatrix} -0.00119 & 0.002346 & 0.0016 \\ 0.004022 & 0.000068 & -0.00097 \\ 0.005152 & -0.00192 & 0.000088 \end{bmatrix} \times \begin{bmatrix} R \\ G \\ B \end{bmatrix}$$ [Mathematical Formula 2]

Then, where a three-color mode is selected by the mode selector 30, the signals of $\lambda 1s$, $\lambda 2s$ and $\lambda 3s$ are supplied to the second color conversion circuit 31 as signals of Rs, GS and Bs. Where a single color mode is selected, any one of these $\lambda 1s$, $\lambda 2s$ and $\lambda 3s$ signals is supplied to the second color conversion circuit 31 as a signal of Rs, Gs or Bs. In the second color conversion circuit 31, signals of Rs, Gs and Bs are converted to Y/C signals (Y, Rs-Y and Bs-Y) and these Y/C signals are supplied via the signal processing circuit 32 and the D/A converter 33 to a monitor and others.

Figure 4:
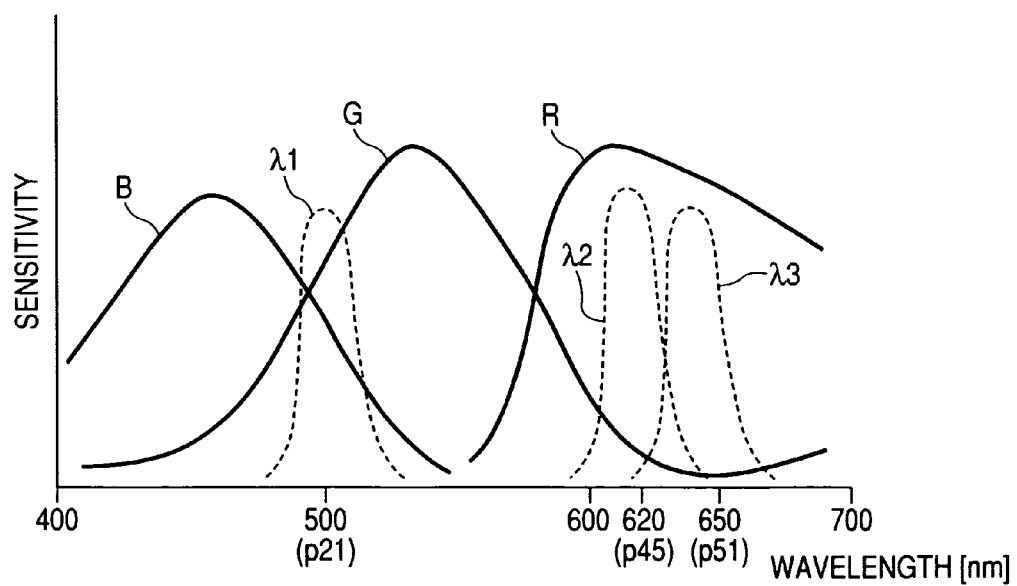
FIG. 4 is a chart showing an example of wavelength ranges of a spectral image together with a spectral sensitivity characteristic of a primary color CCD.
Figures 5, 6:
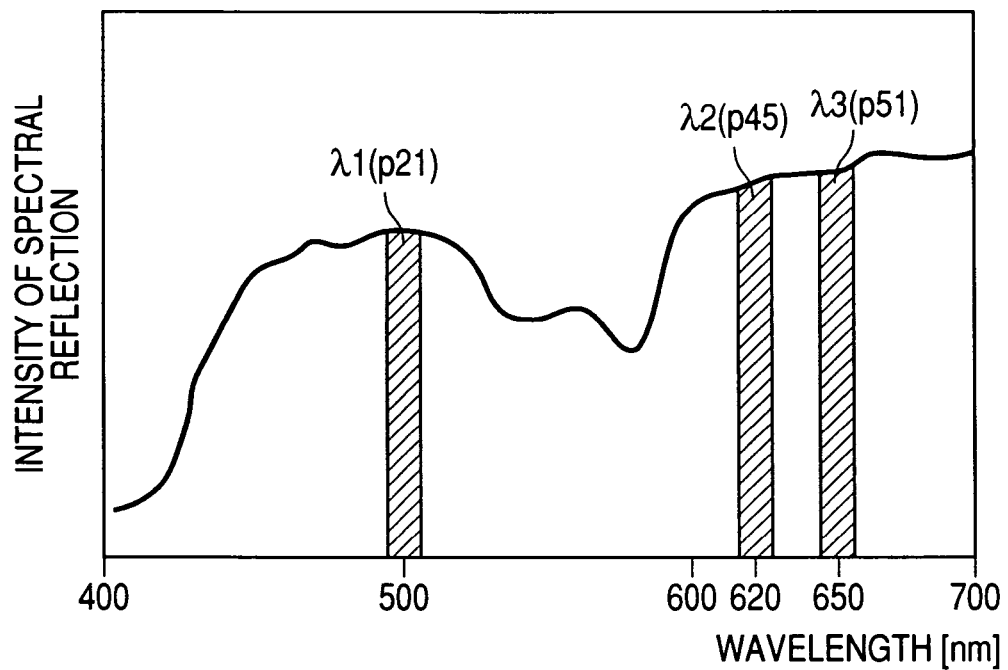
FIG. 5 is a chart showing an example of wavelength ranges of a spectral image together with biological reflectance spectrum.
FIG. 6 is a chart showing a wavelength switching state operated with the wavelength selection switch of the endoscope apparatus shown in FIG. 1.

In such a manner, the spectral image displayed on a monitor, etc., is constituted by color components of the wavelength ranges shown in FIG. 4 and FIG. 5. FIG. 4 is a conceptual diagram in which the three wavelength ranges forming spectral images are superimposed on spectral sensitivity characteristics R, G and B of color filters on the CCD 15 (elementary color-type CCD) (the color filter is not in agreement with the sensitivity graduation of wavelength ranges corresponding to $\lambda 1$, $\lambda 2$ and $\lambda 3$ signals). Further, FIG. 5 is a conceptual diagram in which three wavelength ranges are superimposed on the reflection spectrum of a living body. The wavelengths of p21, p45 and p51 selected as $\lambda 1$, $\lambda 2$ and $\lambda 3$ signals in the embodiment are color signals having the wavelength range of approximately ±10 nm, with the center wavelength being 500 nm, 620 nm and 650 nm in sequence, as illustrated in the diagram. More specifically, displayed are spectral images (moving image and still image) constituted by combinations of colors of the three wavelength ranges.

More specifically, when spectral image is formed and displayed in the state of the selector 26 in which the Y/C signal output from the DSP 25 is supplied to the first color converting circuit 28, and the spectral image forming switch 41j of the operation panel 41 shown in FIG. 2 is pushed, the selector 26 returns the state in which the Y/C signal is supplied to the color signal processing circuit 38 so that ordinary color image of moving or still image is displayed.

The selection of the wavelength ranges $\lambda 1$, $\lambda 2$, and $\lambda 3$ will now be explained. In the present embodiment, as shown in FIG. 2, as the wavelength sets of $\lambda 1$, $\lambda 2$, and $\lambda 3$, for example, a standard set a composed of 400, 500, 600 (nm, the same applies hereinafter.), a blood vessel B1 set b composed of 470, 500, 670 for describing a blood vessel, a blood vessel B2 set c composed of 475, 510, 685 for also describing a blood vessel, a tissue E1 set d composed of 440, 480, 520 for describing a specific tissue, a tissue E2 set e composed of 480, 510, 580 for also describing a specific tissue, a hemoglobin set f composed of 400, 430, 475 for describing differences between the oxyhemoglobin and the deoxyhemoglobin, a blood-carotene set g composed of 415, 450, 500 for describing differences between blood and carotene, and a blood-cytoplasm set h composed of 420, 550, 600 for describing differences between blood and cytoplasm, totally eight wavelength sets are stored in the first area 42a of the wavelength set memory 42 shown in FIG. 2 as the default wavelength sets.

At the factory shipment of the electronic endoscope apparatus, the default wavelength sets stored in the first area 42a are also stored in a second area 42b of the wavelength set memory 42, and after then, when the apparatus is powered on to start up for the first time, the default wavelength sets stored in the second area 42b are selected by the microcomputer 35. And, when the spectral image forming switch 41j of the operation panel shown in FIG. 2 is operated, the standard set a in the selected wavelength sets describe above is displayed in the wavelength information display area 34s on the monitor 34 shown in FIGS. 3A through 3C. In this case, if the mode changeover switch 41d is operated to select the three color mode, each of the parameters corresponding to the wavelengths $\lambda 1$=400 nm, $\lambda 2$=500 nm, and $\lambda 3$=600 nm in the standard set a is read out from the memory 36 and then inputted to the color space conversion processing circuit 29. The color space conversion processing circuit 29 conducts the matrix operation described above using the inputted parameters to form the spectral image signals $\lambda 1s$, $\lambda 2s$, and $\lambda 3s$. And, the spectral image composed of the spectral image signals $\lambda 1s$, $\lambda 2s$, and $\lambda 3s$ is displayed on the monitor 34.

Further, the operator of the apparatus such as a clinical doctor can freely select another wavelength set of the default wavelength sets b through h by operating the set selecting switch 41a provided on the operation panel 41 shown in FIG. 2, and the microcomputer 35 displays the wavelength set thus elected in the wavelength information display area 34s on the monitor 34. Incidentally, also in this case, each of the parameters corresponding to the wavelengths $\lambda 1$, $\lambda 2$, and $\lambda 3$ of the selected wavelength set is read out from the memory 36 and then inputted to the color space conversion processing circuit 29 by the microcomputer 35. The color space conversion processing circuit 29 conducts the matrix operation described above using the inputted parameters to form the spectral image signals $\lambda 1s$, $\lambda 2s$, and $\lambda 3s$. And, the spectral image composed of the spectral image signals $\lambda 1s$, $\lambda 2s$, and $\lambda 3s$ is displayed on the monitor 34.

Note that, as shown in FIG. 2, the set selecting switch 41a is composed of an ascending switch having an up-triangle operating section and a descending switch having a down-triangle operating switch, and every time the former is pushed once, the selection of the wavelength set is sequentially changed as a→h→g . . . , on the contrary, every time the latter is pushed once, the selection of the wavelength set is changed as a→b→c . . . in sequence.

Further, when either one of the wavelength sets a through h is selected, the operator can change each of the wavelength ranges $\lambda 1$, $\lambda 2$, and $\lambda 3$ of the selected wavelength set to a desired value by operating the wavelength selection switch 41b. In changing the wavelength ranges, the change amount of the wavelength can be changed by the changeover width setting switch 41c. Namely, by rotating the knob of the changeover width setting switch 41c, the amount of change can be set to, for example, 1 nm for almost continuous change, 5 nm for stepwise change, 10 nm, or 20 nm, thus the continuous change or stepwise change can be selected. Note that, by changing by 1 nm, for example, 301 wavelength ranges are defined in a range of 400 nm through 700 nm, and the matrix data (p'1 through p'301) corresponding to the 301 wavelength ranges need to be prepared.

FIG. 6 shows selection of the wavelength range. When the 5 nm width is set, the changeover is in order of 400→405→410 as shown in the changeover of $\lambda 1$, and when the 20 nm width is set, the changeover is made in order of 600→620→640 as shown in the changeover of $\lambda 3$, and these values are displayed at a wavelength information display area 34s on the monitor 34. This is advantageous in that a wavelength range for searching a target can be set easily.

Figure 3A:
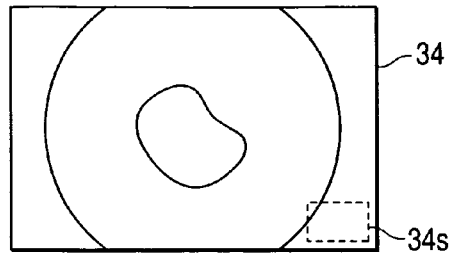
FIGS. 3A through 3C are diagrams showing a wavelength information displaying area in a monitor of the endoscope apparatus shown in FIG. 1 and a display sample.
Figure 3B:
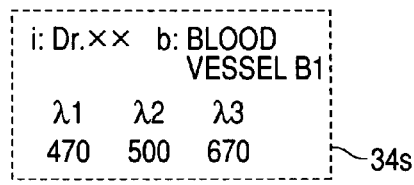
Figure 3C:
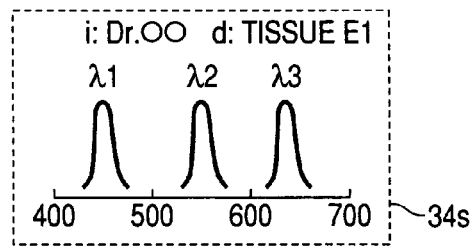

FIGS. 3A through 3C show display appearance in the wavelength information display area 34s in detail. In the present embodiment, as shown in FIG. 3A, the wavelength information is displayed in the wavelength information display area 34s prepared to a lower right section of the monitor 34 with a help of character generation in the signal processing circuit 32. Namely, as shown in FIG. 3B, in the wavelength information display section 34s, the value (nm) of the selected wavelength is displayed under the letters such as $\lambda 1$, $\lambda 2$, $\lambda 3$ and soon. Alternatively, as shown in FIG. 3C, the selected wavelength ranges can visually be displayed with a movable graph (corresponding to FIG. 4) with wavelength on the horizontal axis and sensitivity on the vertical axis.

Note that the process of changing the wavelength ranges $\lambda 1$, $\lambda 2$, and $\lambda 3$ of the wavelength set to desired values, as described above, is executed by storing temporary data to the working area 42d of the wavelength set memory 42.

The mode changeover switch 41d shown in FIG. 2 is for switching between the single color mode and the three color mode, and if the mode changeover switch 41d is operated in the three color mode, the mode is switched to the single color mode in which all of the wavelength ranges $\lambda 1$, $\lambda 2$, and $\lambda 3$ are set to the same value like 470, 470, 470, by the microcomputer 35. And, the common wavelength range is displayed on the monitor 34 as shown in FIG. 7. Note that regarding the common wavelength range, a desired value can be selected by operating the wavelength selection switch 41b described above.

Note here that the functions of some switches on the operation panel 41 can be replaced with key functions of the keyboard, or all of the functions can be replaced with key functions of the keyboard.

As described above, if the wavelength ranges $\lambda 1$, $\lambda 2$, and $\lambda 3$ are changed regarding some of the wavelength sets a through h, the revised wavelength sets a through h including the changes are overwritten in the second area 42b of the wavelength set memory 42 by the microcomputer 35 in response to the operation of the storing switch 41h provided on the operation panel shown in FIG. 2. Such a storing function is convenient in the case in which the spectral image is immediately formed and then displayed using the revised wavelength sets a through h.

Further, the revised wavelength sets a through h thus formed as described above are newly stored in a third area 42c of the wavelength set memory 42 by the microcomputer 35 when, for example, the storing switch 41h and the doctor page switch 41g provided on the operation panel 41 shown in FIG. 2 are operated simultaneously. In this case, a guide sign is displayed on the monitor 34 shown in FIGS. 3A through 3C for prompting the operator who executes the storing operation to input his or her name. Then, the name of "Dr. xx," for example, is inputted using the input section 43 such as a keyboard shown in FIG. 1. The microcomputer 35 stores the revised wavelength sets a through h to the third area 42c in conjunction with the inputted name. In the present embodiment, as an example, up to ten groups of wavelength sets a through h can be stored in conjunction with names of respective operators of the apparatus.

The wavelength sets a through h stored in the third area 42c of the wavelength set memory 42 can be read out from the third area 42c and used by operating the doctor page switch 41g provided on the operation panel 41. Namely, every time the doctor page switch 41g is operated once, the wavelength sets are sequentially selected and read out from the third area 42c, and stored to the second area 42b, the changed wavelength storing area, in such a manner as the first group of wavelength sets a through h, the second group of wavelength sets a through h, the third group of wavelength sets a through h, . . . by the microcomputer 35. And, each of the parameters corresponding to the wavelength ranges $\lambda 1$, $\lambda 2$, and $\lambda 3$ of the stored wavelength sets is read out from the memory 30 by the microcomputer 35. The spectral image formation of with these parameters is carried out similarly to the process described above.

Note that regarding the wavelength sets a through h, as shown in FIGS. 3B and 3C, in the wavelength information display area 34s of the monitor 34, the name of the composer and the name of the set are displayed such a manner as "Dr. xx, b. BLOOD VESSEL B1" together with "i" indicating the spectral image formation, for example. Thus, it can be confirmed what kind of wavelength set the spectral image is formed and displayed based on.

Although the most suitable wavelength ranges $\lambda 1$, $\lambda 2$, and $\lambda 3$ for forming and displaying spectral image easy to be clinically observed are often different among the operators of the apparatus such as doctors, by arranging that a group of wavelength sets a through h are formed, then stored, and can be read out to be used for each of the operators of the apparatus as described above, the spectral image easiest for each operator to observe can quickly and simply be formed.

Note that in performing the display like "Dr. xx, b. BLOOD VESSEL B1" regarding the wavelength set as described above, it is convenient to display with different colors, namely, with white, for example, if the wavelength set is the same as the default one, or with green, for example, if the wavelength set is changed from the default one, to know the history of the wavelength set.

Further, the wavelength sets a through h read out from the third area 42c of the wavelength set memory 42 can further be changed in a part or the whole of wavelength ranges $\lambda 1$, $\lambda 2$, and $\lambda 3$ in the same manner as the case in which the default wavelength sets a through h read out from the first area 42a are changed. The wavelength sets a through h thus changed are overwritten in the third area 42c of the wavelength set memory 42 shown in FIG. 1 by the microcomputer 35 in response to operation of the storing switch 41h provided on the operation panel 41. Namely, if the wavelength sets are the first group of wavelength sets formed by, for example, Dr. xx, then the changed wavelength sets a through h are stored as the revised first group of wavelength sets.

Further, the wavelength sets a through h changed as described above can also be stored to the third area 42c of the wavelength set memory 42 shown in FIG. 1 as a new group of wavelength sets by simultaneously operating the storing switch 41h and the doctor page switch 41g provided on the operation panel 41. In this case, a guide sign is also displayed on the monitor 34 shown in FIGS. 3A through 3C for prompting the operator who executes the storing operation to input his or her name. Then, the name of "Dr. yy," for example, is inputted using the input section 43 such as a keyboard shown in FIG. 1. The microcomputer 35 stores the new wavelength sets a through h to the third area 42c in conjunction with the inputted name. Accordingly, it becomes possible for the operator of the apparatus without enough clinical experience to easily form the wavelength sets by partially diverting the wavelength sets a through h created by the operator of the apparatus with broad clinical experience.

Note that it can be arranged that, instead of simultaneously operating the storing switch 41h and the doctor page switch 41g as described above, the confirmation of "OVERWRITE?" is displayed when only the storing switch 41h is operated, and if approval is inputted from the input section 43, the wavelength sets are overwritten as the wavelength sets of the group from which the wavelength sets are read out, and if disapproval is inputted, the wavelength sets are newly stored as wavelength sets of a different group from the group from which the wavelength sets are read out.

The reset operation of the wavelength sets stored in the second area 42b of the wavelength set memory 42 will hereinafter be explained. After changing the default wavelength sets stored in the second area 42b as described above and forming and then displaying the spectral image based on the changed wavelength sets, if the all reset switch 41e provided on the operation panel 41 is operated, the microcomputer 35 reads out the default wavelength sets stored in the first area 42a of the wavelength set memory 42 and stores them to the second area 42b.

It is desirable that the reset operation is always executed after the spectral image is formed and then displayed. By thus operated, since the formation of new wavelength sets based on the wavelength sets stored in the second area 42b is always executed based on the default wavelength sets no matter who becomes the operator of the apparatus, the confusion in forming the new wavelength sets caused by existence of a plurality of base wavelength sets can be prevented.

Further, after changing the default wavelength sets stored in the second area 42b as described above and forming and then displaying the spectral image based on the changed wavelength sets, if the partial reset switch 41f provided on the operation panel shown in FIG. 2 is operated, the microcomputer 35, as a substitution for the group of wavelength set (either one of a through h) used for forming the spectral image, stores the same group of wavelength set (either one of a through h) in the default wavelength sets stored in the first area 42a to the second area 42b. By thus operated, the confusion in judging the most suitable wavelength ranges $\lambda 1$, $\lambda 2$, and $\lambda 3$ caused by too much changes on a specific wavelength set (either one of a through h) can be cleared up by reset the wavelength set with the default wavelength set forming a reference.

The reset operation of the wavelength sets stored in the third area 42c of the wavelength set memory 42 will hereinafter be explained. After changing the wavelength sets for every operator of the apparatus stored in the third area 42c as described above and forming and then displaying the spectral image, if the all reset switch 41e provided on the operation panel 41 shown in FIG. 2 is operated, the microcomputer 35 reads out the default wavelength sets stored in the first area 42a of the wavelength set memory 42 and stores them to the third area 42c.

Alternatively, after changing the wavelength sets for every operator of the apparatus stored in the third area 42c as described above and forming and then displaying the spectral image based on the changed wavelength sets, if the partial reset switch 41f provided on the operation panel shown in FIG. 2 is operated, the microcomputer 35, as a substitution for the group of wavelength set (either one of a through h) used for forming the spectral image, stores the same group of wavelength set (either one of a through h) in the default wavelength sets stored in the first area 42a to the third area 42c.

By conducting either one of the reset operations, the confusion in judging the most suitable wavelength ranges $\lambda 1$, $\lambda 2$, and $\lambda 3$ caused by too much changes on wavelength ranges $\lambda 1$, $\lambda 2$, and $\lambda 3$ of a specific or plural wavelength sets a through h can be cleared up by reset with the default wavelength set forming a reference.

FIG. 8 shows another example where a wavelength set is changed by the set selecting switch 41a. In the example, it is constituted so that a predetermined number of sets (4 sets, 5 sets and others) are cyclically changed by the set selecting switch 41a. For example, as shown in this figure, "a" (standard) set, "b" (blood vessel B1) set, "c" (blood vessel B2) set and "d" (tissue E1) set (predetermined number of sets) are set so that these four sets can be changed in sequence and cyclically. Further, in place of these "b" to "d" sets, other sets, or "e" to "h" (tissue E2, hemoglobin, blood-carotene, blood-cytoplasm and others) are selected, thereby making it possible to change wavelength sets to be changed. Therefore, a wavelength set can be selected easily by setting frequently-used wavelength sets.

In the above embodiment, the wavelength range from 400 nm to 700 nm is divided into 61 wavelength ranges for selection. A wavelength range including an infrared region or a wavelength set made up of only the infrared region may be selected as the wavelength range of $\lambda 1$, $\lambda 2$ or $\lambda 3$, thereby making it possible to obtain a spectral image close to an image obtained by infra-red radiation in the prior art, without using a cut filter of visible light region. Further, in a conventional endoscope, fluorescence emitted from cancerous tissues and others through radiation of exciting light is photographed. In the present invention, however, as the wavelength set of the above-described λ1, λ2 and λ3, a set adjusted to the fluorescence wavelength can be selected to form a spectral image which targets a fluorescence-emitting portion. This is advantageous in that no cut filter for exciting light is needed.

In addition, in a conventional endoscope, a pigment such as indigo or pioctanine is sprayed to a body to be observed, thereby photographing tissues dyed with the sprayed pigment. In the present invention, however, a wavelength range capable of visualizing tissues dyed by spraying pigments is selected as the wavelength set of the above-described λ1, λ2 and λ3, thereby making it possible to obtain a spectral image equivalent to an image by spraying pigments without actually spraying pigments.

Figure 9:
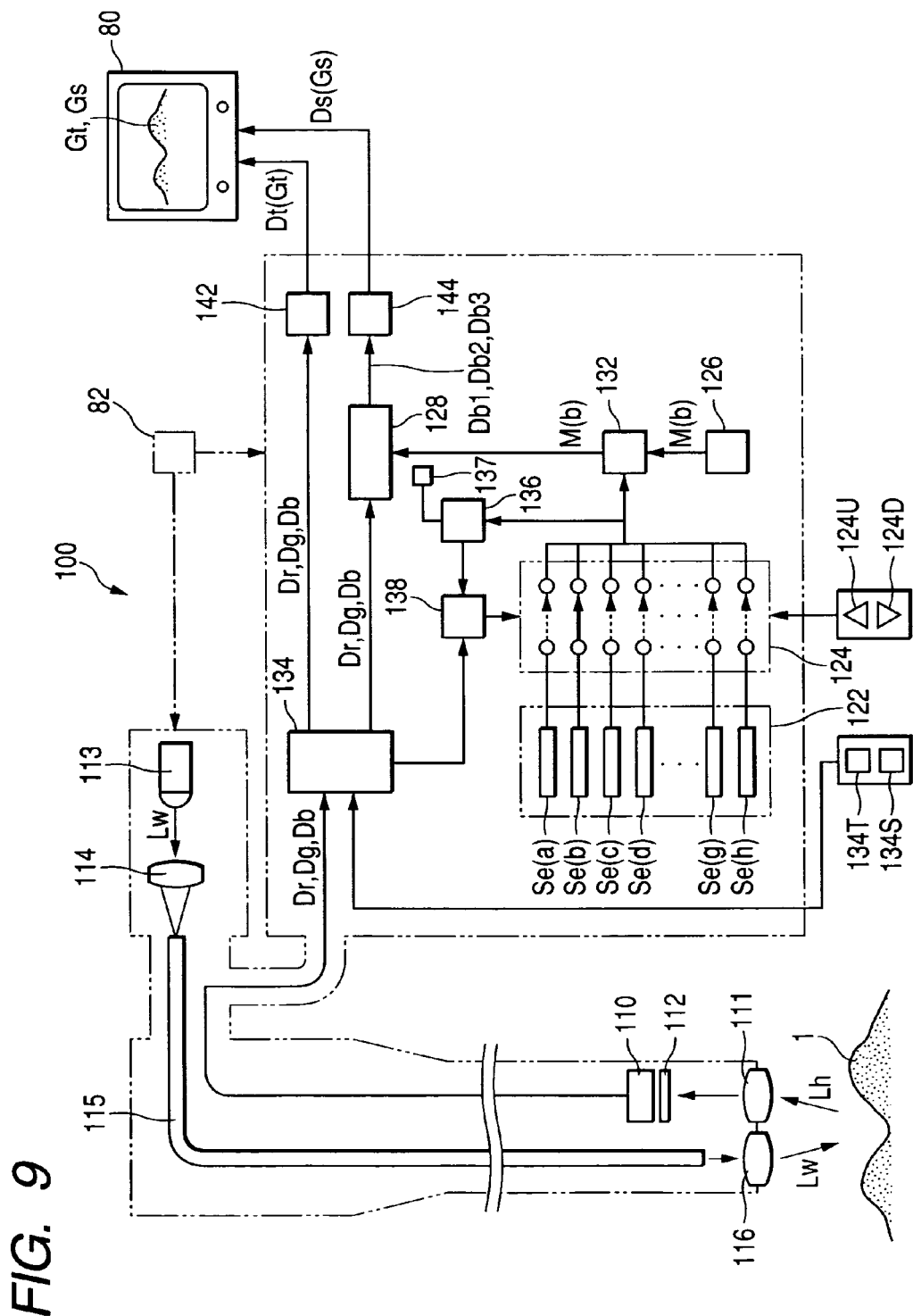
FIG. 9 is a block diagram showing a schematic configuration of an electronic endoscope apparatus according to an embodiment of the invention.
Figure 10:
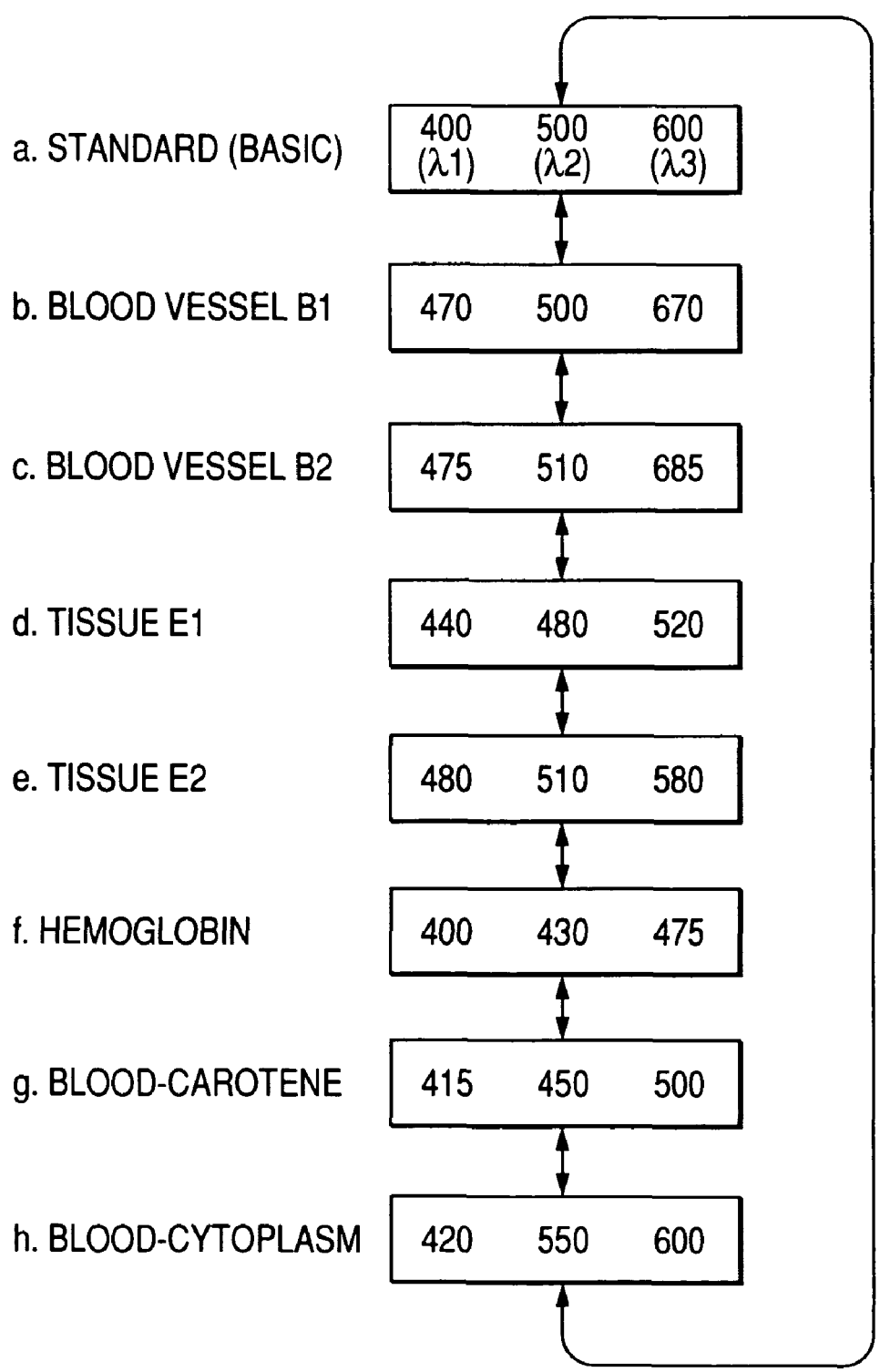
FIG. 10 is a diagram showing a specific example of wavelength sets.

Hereinafter, other embodiments of the invention are described with reference to the accompanying drawings. FIG. 9 is a block diagram showing a schematic configuration of an electronic endoscope apparatus according to an embodiment of the invention, and FIG. 10 is a chart showing a specific example of wavelength sets.

An electronic endoscope apparatus 100 according to the embodiment of the invention shown in FIG. 9 is equipped with an image pickup section 110 for taking an image of a biological mucous membrane 1 through a color mosaic filter 112 to obtain wide-band spectral image data Dr, Dg, and Db in a red wavelength band, a green wavelength band, and a blue wavelength band forming an ordinary image of the biological mucous membrane 1, a wavelength set storing section 122 for storing wavelength sets Se(a), Se(b), . . . each defining wavelength bands (explained to be narrow-bands) of narrow-band spectral images forming a diagnostic image of the biological mucous membrane 1, a wavelength set selecting section 124 for selecting one of the wavelength sets to be used for the operation of the spectral image estimation described above out of the wavelength sets Se (a), Se (b), . . . stored in the wavelength set storing section 122, a matrix data storing section 126 storing spectral reflection estimation matrix data M to be used for the operation of spectral image estimation regarding the biological mucous membrane 1, a spectral image estimation calculating section 128 for obtaining narrow-band spectral image data Db1, Db2, and Db3 of the biological mucous membrane 1 respectively corresponding to wavelength bands λb1, λb2, λb3 designated by the wavelength set selected by the wavelength set selecting section 124, the wavelength set Se (b), for example, by the spectral image estimation calculation based on the wide-band spectral image data Dr, Dg, and Db and the spectral reflection estimation matrix data corresponding to the selected wavelength set, Se (b), for example, a matrix data extracting section 132 for referring to the wavelength set selected by the wavelength set selecting section 124, the wavelength set Se(b), for example, extracting the spectral reflection estimation matrix data M corresponding to the wavelength set, M(b) for example, and outputting the extracted spectral reflection estimation matrix data M(b) to the spectral image estimation calculating section 128.

Note that the ordinary image described above is a wide-band spectral image composed of the three kinds of wide-band spectral images expressed by the wide-band spectral image data Dr, Dg, and Db. In contrast, the diagnostic image is a narrow-band spectral image composed of the three kinds of narrow-band spectral images expressed by the narrow-band spectral image data Db1, Db2, and Db3.

Further, the electronic endoscope apparatus 100 is equipped with a display mode switching section 134 capable of displaying by switching between an ordinary image display mode for displaying the ordinary image of the biological mucous membrane 1 composed using the wide-band spectral image data Dr, Dg, and Db on a display device 80 and a diagnostic image display mode for displaying the diagnostic image Gs composed using the narrow-band spectral image data Db1, Db2, and Db3 on the display device 80, a latest wavelength set storing section 136 for storing the wavelength set selected most recently by the wavelength set selecting section 124 during the diagnostic image display mode is selected by switching, and an initial display setting section 138 for displaying the diagnostic image corresponding to the wavelength set stored in the latest wavelength set storing section 136 in response to the display mode switching section 134 switching from the ordinary image display mode to the diagnostic image display mode.

As described above, the electronic endoscope apparatus 100 can display the ordinary image Gt, which is a wide-band image of the biological mucous membrane 1, and the diagnostic image Gs, which is a narrow-band spectral image of the biological mucous membrane 1 obtained by the spectral image estimation operated by the spectral image estimation calculation section 128 based on the wavelength set selected form the plural kinds of wavelength sets stored in the wavelength set storing section 122, on the display device 80 alternatively by switching. Further, the electronic endoscope apparatus 100 is equipped with the latest wavelength set storing section 136 and is configured to display diagnostic image Gs corresponding to the wavelength set stored in the latest wavelength set storing section 136 by an operation of the initial display setting section 138 when the image to be displayed on the display device 80 is switched from the ordinary image Gt to the diagnostic image Gs by the display mode switching section 134.

The electronic endoscope apparatus 100 is further equipped with an ordinary image data generating section 142 for composing the wide-band spectral image data Dr, Dg, and Db to generate the ordinary image data Dt expressing the ordinary image, diagnostic image data generating section 144 for composing the narrow-band spectral image data Db1, Db2, and Db3 to generate the diagnostic image data Ds expressing the diagnostic image, and a controller 82 for controlling timing and synchronization of all operations of the electronic endoscope apparatus 100.

Note that the spectral reflection estimation matrix data is previously determined in accordance with the spectral reflection characteristics of the biological mucous membrane through an experiment or the like. By conducting the spectral image estimation calculation of the spectral reflection estimation matrix data corresponding to a specific wavelength set and the wide-band spectral image data Dr, Dg, and Db, the narrow-band spectral image data expressing the narrow-band spectral images of the biological mucous membrane 1 in each of the wavelength bands designated by the specific wavelength set can be obtained.

Further, the wavelength set selecting section 124 is connected to a forward switching button 124U and a reverse switching button 124D, which are cyclic switches for selecting the wavelength set, and one of the wavelength sets Se(a), Se(b), . . . stored in the wavelength set storing section 122 is selected in this order or in the reverse order every time the forward switching button 124U or the reverse switching button 124D is operated.

The display mode switching section 134 is connected to an ordinary image display button 134T and a diagnostic image display button 134S, and the display mode is switched to the ordinary image display mode in response to operation of the ordinary image display button 134T while the display mode is switched to the diagnostic image display mode in response to operation of the diagnostic image display button 134S.

Namely, when the ordinary image display button 134T is pushed, the display mode switching section 134 transfers the wide-band spectral image data Dr, Dg, and Db obtained by the image taking operation of the image pickup section 110 to the ordinary image data generating section 142, and then the ordinary image data generating section 142 composes the wide-band spectral image data Dr, Dg, and Db thus transferred to generate the ordinary image data Dt. And, the display device 80, which receives the ordinary image data Dt transferred from the ordinary image data generating section 142, displays the ordinary image Gt.

In contrast, when the diagnostic image display button 134S is pushed, the display mode switching section 134 transfers the wide-band spectral image data Dr, Dg, and Db to the spectral image estimation calculating section 128, and then the spectral image estimation calculating section 128 generates narrow-band spectral image data Db1, Db2, and Db3 by the spectral image estimation calculation base on the wide-band spectral image data Dr, Dg, and Db thus transferred. And then, the diagnostic image data generating section 144, which receives the narrow-band spectral image data Db1, Db2, and Db3, composes the image data to generate the diagnostic image data Ds expressing the diagnostic image of the biological mucous membrane 1. After then, the display device 80, which receives the diagnostic image data Ds output from the diagnostic image data generating section 144, displays the diagnostic image Gs.

The latest wavelength set storing section 136 includes a backup power supply 137, which is a backup section for making it possible to keep the storage of the wavelength set in the latest wavelength set storing section 136 even when the drive power of the electronic endoscope apparatus 100 is in the OFF state.

An operation of the electronic endoscope apparatus will hereinafter be described.

White light Lw emitted from a lighting source 113 is condensed through a condenser lens 114, inputted to one end of a light guide 115, and then outputted from the other end of the light guide 115. The white light Lw outputted from the other end of the light guide 115 illuminates the biological mucous membrane 1 after passing through a lighting lens 116.

Reflected light Lh, which is reflected on the biological mucous membrane 1 in accordance with the irradiation of the white light Lw and has an image of the biological mucous membrane 1, is dispersed through the color mosaic filter 112 disposed in front of acceptance surfaces of the solid image pickup elements equipped to the image pickup section 110, and is focused with an image on the acceptance surfaces described above through an imaging optics 111.

The image pickup section 110 takes the image dispersed and focused on the acceptance surfaces, and obtains the wide-band spectral image data Dr, Dg, and Db expressing the wide-band spectral images Gr, Gg, and Gb showing the biological mucous membrane 1 in the red wavelength band, the green wavelength band, and the blue wavelength band, respectively.

When the ordinary image display mode is selected by operating the ordinary image display button 134T, the ordinary image Gt composed using the wide-band spectral image data Dr, Dg, and Db is displayed on the display device 80. On the contrary, when the diagnostic image display mode is selected by operating the diagnostic image display button 134S, the diagnostic image Gs composed of the narrow-band spectral image data Db1, Db2, and Db3 obtained by the spectral image estimation calculation based on the wide-band spectral image data Dr, Dg, and Db is displayed on the display device 80.

Switching of the image display mode will hereinafter be explained in detail.

When, for example, the forward switching button 124U is pushed while the diagnostic image display mode is selected by pushing the diagnostic image display button 134S, the wavelength set selecting section 124 selects the wavelength set Se (c), which is the posterior wavelength set of the wavelength set Se (b) presently selected, out of the plural kinds of wavelength sets stored in the wavelength set storing section 122.

And, the data of the wavelength set Se (c) representing plural kinds of wavelength bands $\lambda c1$, $\lambda c2$, and $\lambda c3$ is inputted to the matrix data extracting section 132.

As shown in FIG. 10, as the wavelength set, a standard (basic) wavelength set (a) composed of, for example, 400 (center wavelength), 500, 600 (in the order of $\lambda 1$, $\lambda 2$, $\lambda 3$, unit: nm), a blood vessel B1 wavelength set (b) composed of 470, 500, 670, and a blood vessel B2 wavelength set (c) composed of 475, 510, 685, for describing blood vessels, a tissue E1 wavelength set (d) composed of 440, 480, 520, and a tissue E2 wavelength set (e) composed of 480, 510, 580 for describing specific tissues, a hemoglobin wavelength set (f) composed of 400, 430, 475 for describing differences between the oxyhemoglobin and the deoxyhemoglobin, a blood-carotene wavelength set (g) composed of 415, 450, 500 for describing differences between blood and carotene, a blood-cytoplasm wavelength set (h) composed of 420, 550, 600 for describing differences between blood and cytoplasm, and so on are stored therein, and a desired one of these wavelength sets is sequentially selected by the wavelength set selecting section 124 in a cyclic manner. And, the selected wavelength set is inputted in the matrix data extracting section 132.

The matrix data extracting section 132 looks up the wavelength set Se(c) inputted thereto to extract the spectral reflection estimation matrix data M(c) for estimating, by an operation, the spectral reflection intensity in each of the wavelength bands $\lambda c1$, $\lambda c2$, and $\lambda c3$ designated by the wavelength set Se (c) from the matrix data storing section 126, and outputs the spectral reflection estimation matrix data M(c) to the spectral image estimation calculating section 128.

The spectral image estimation calculating section 128 obtains narrow-band spectral image data Dc1, Dc2, and Dc3 expressing the narrow-band spectral images Gc1, Gc2, and Gc3 of the biological mucous membrane 1 in the wavelength bands $\lambda c1$, $\lambda c2$, and $\lambda c3$, respectively, by the spectral image estimation calculation, which is a matrix calculation shown in formula (1) below using the spectral reflection estimation matrix data M(c) inputted from the matrix data extracting section 132 and the wide-band spectral image data Dr, Dg, and Db inputted through the display mode switching section 134.

An example of the spectral reflection estimation matrix data stored in the matrix data storing section 126 is as shown in Table 1 above.

And, in the spectral image estimation calculating section 128, the matrix calculation as shown in mathematical formula 3 below is executed using the coefficients kpr, kpg, and kpb mentioned above and the wide-band spectral image data Dr, Dg, and Db outputted from the image pickup section 110. Note that the three by three matrix composed of the coefficients kpr, kpg, and kpb described above corresponds to the spectral reflection estimation matrix data. Further, the letters R, G, and B in the formula correspond to the wide-band spectral image data Dr, Dg, and Db, respectively.

$$\begin{bmatrix} \lambda 1 \\ \lambda 2 \\ \lambda 3 \end{bmatrix} = \begin{bmatrix} k1r & k1g & k1b \\ k2r & k2g & k2b \\ k3r & k3g & k3b \end{bmatrix} \times \begin{bmatrix} R \\ G \\ B \end{bmatrix}$$ [Mathematical Formula 3]

Namely, for example, the parameter p21 (center wavelength: 500 nm), p45 (center wavelength: 620 nm), and p51 (center wavelength: 650 nm) shown in Table 1 are selected as λ1, λ2, and λ3, respectively, it is enough to substitute the parameters (kpr, kpg, and kpb) with the values in p21 (−0.00119, 0.002346, 0.0016), p45 (0.004022, 0.000068, −0.00097), and p51 (0.005152, −0.00192, 0.000088).

The condition in which the values of the parameters are inputted in mathematical formula 3 above will be described below.

$$\begin{bmatrix} \lambda 1 \\ \lambda 2 \\ \lambda 3 \end{bmatrix} \begin{bmatrix} -0.00119 & 0.002346 & 0.0016 \\ 0.004022 & 0.000068 & -0.00097 \\ 0.005152 & -0.00192 & 0.000088 \end{bmatrix} \times$$ [Mathematical Formula 4]

$$\begin{bmatrix} R \\ G \\ B \end{bmatrix}$$

The diagnostic image composed of the narrow-band spectral images obtained by such a spectral image estimation calculation is composed of the color components of the wavelength bands shown in FIGS. 4 and 5. Namely, FIG. 4 is a schematic diagram composed by overlapping the spectral sensitivity characteristics of the mosaic filter composed of primary color type of color filters and the three wavelength bands forming the diagnostic image (the sensitivity scale of the color filters and the sensitivity scale of the wavelength bands λ1, λ2, and λ3 do not correspond to each other). Further, FIG. 5 is a schematic diagram composed by overlapping the three wavelength bands forming the diagnostic image on the intensity distribution of spectral reflection of the biological mucous membrane, and the parameters p21, p45, and p51 selected as λ1, λ2, and λ3 denote wavelength bands having center wavelengths of 500 nm, 620 nm, 650 nm, respectively, and ranges of about ±10 nm as shown in the drawing. The diagnostic image is composed of a combination of the colors in these three wavelength bands.

Namely, the narrow-band spectral image data Dc1, Dc2, and Dc3 corresponding to λ1, λ2, and λ3 in the above formula obtained by the spectral image estimation calculation are inputted to the diagnostic image data generating section 144, and then the diagnostic image data Ds(c) is composed by the diagnostic image data generating section 144 from the narrow-band spectral image data Dc1, Dc2, and Dc3, and then the diagnostic image Gs (c) expressed by the diagnostic image data Ds(c) is displayed on the display device 80.

Note that, every time the forward switching button 124U or the reverse switching button 124D is operated, the operation for forming the diagnostic image corresponding to the selected wavelength set is executed, thus the different kinds of diagnostic images are displayed in sequence.

Meanwhile, the ordinary color image can be displayed by switching the display mode switching section 134 to the ordinary image display mode.

Note that JP-A-2003-93336 or Yoichi Miyake "Analysis and Evaluation of Digital Color Images," University of Tokyo Press can be referred for the method of obtaining the narrow-band spectral images utilizing the spectral image estimation calculation.

The operation of displaying the diagnostic image corresponding to the wavelength set stored in the latest wavelength set storing section 136 in response to the display mode switching section 134 switching from the ordinary image display mode to the diagnostic image display mode will hereinafter be explained.

In the diagnostic image display mode, for example, when the wavelength set Se(g) is selected by the wavelength set selecting section 124, the data designating the wavelength set Se(g) is transferred from the wavelength set selecting section 124 to the matrix data extracting section 132, and at the same time, the data designating the wavelength set Se(g) is also stored to the latest wavelength set storing section 136. And, the diagnostic image Gs(g) composed using the spectral reflection estimation matrix data M (g) corresponding to the wavelength set Se(g) as described above is displayed on the display device 80.

After then, when the ordinary image display button 134T is operated to switch the mode from the diagnostic image display mode to the ordinary image display mode, the following condition takes place. Namely, although the condition in which the diagnostic image Gs(g) is displayed on the display device 80 is switched to the condition in which the ordinary image is displayed, the latest wavelength set storing section 136 keeps the state of storing the wavelength set Se(g).

Subsequently, when the diagnostic image display button 134S is operated to switch the mode to the diagnostic image display mode, the initial display setting section 138 detects that the mode has been switched from the ordinary image display mode to the diagnostic image display mode. And, the initial display setting section 138, with reference to the wavelength set Se(g) stored in the latest wavelength set storing section 136, controls the wavelength set selecting section 124 to become in the state of selecting the wavelength set Se(g).

Thus, the diagnostic image Gs (g) composed using the spectral reflection estimation matrix data M(g) corresponding to the wavelength set Se(g) is displayed similarly to the above case.

Namely, when the display is switched from the ordinary image to the diagnostic image, the matrix data extracting section 132 extracts the spectral reflection estimation matrix data M(g) corresponding to the wavelength set Se(g) stored in the latest wavelength set storing section 136, and outputs the spectral reflection estimation matrix data M(g) thus extracted to the spectral image estimation calculating section 128. And then, the spectral image estimation calculation and so on are executed thereon similarly to the above, and the diagnostic image Gs(g) is displayed on the display device 80.

After displaying the diagnostic image Gs (g), a desired one of the diagnostic images corresponding to the wavelength set selected by operating either of the forward switching button 124U or the reverse switching button 124D can be displayed.

Although in the embodiment described above, the cyclic switching method in which one of the wavelength set Se(a), Se(b), . . . Se(h) is sequentially selected alternatively in the forward direction and the reverse direction is adopted as the means for selecting the wavelength set, it is not limited to such a case.

For example, in selecting one of the wavelength sets Se (a), Se(b), . . . Se(h) simply in sequence in the forward direction and the reverse direction instead of selecting in a cyclic manner as described above, a limited sequential switching method in which the wavelength set Se(a) is not selected next to the wavelength set Se(h) or the wavelength set Se(h) is not selected next to the wavelength set Se (a) can be adopted. Further, the random switching method provided with individual push buttons capable of selecting each of the wavelength sets Se(a), Se(b), . . . Se(h) at random can also be adopted.

Even if the limited sequential switching method or the random switching method is adopted, the same advantage as the case with the cyclic switching method, namely the advantage that the operation for switching between the ordinary image and the desired diagnostic image can more easily be executed by displaying the diagnostic image corresponding to the wavelength set stored in the latest wavelength set storing section upon switching from the ordinary image to the diagnostic image, can be obtained.

Note that any method can be adopted as the configuration in which the wavelength set selected most recently is stored and the diagnostic image corresponding to the latest wavelength set is displayed upon switching the display of the image from the ordinary image to the diagnostic image, and the configuration is not limited to one using the latest wavelength set storing section and the initial display setting section described above.

As a method of realizing the function that the wavelength set selected most recently is stored and the diagnostic image corresponding to the latest wavelength set is displayed upon switching the display of the image from the ordinary image to the diagnostic image, methods described in the following modified embodiments can be adopted.

First Modified Embodiment

Figure 11:
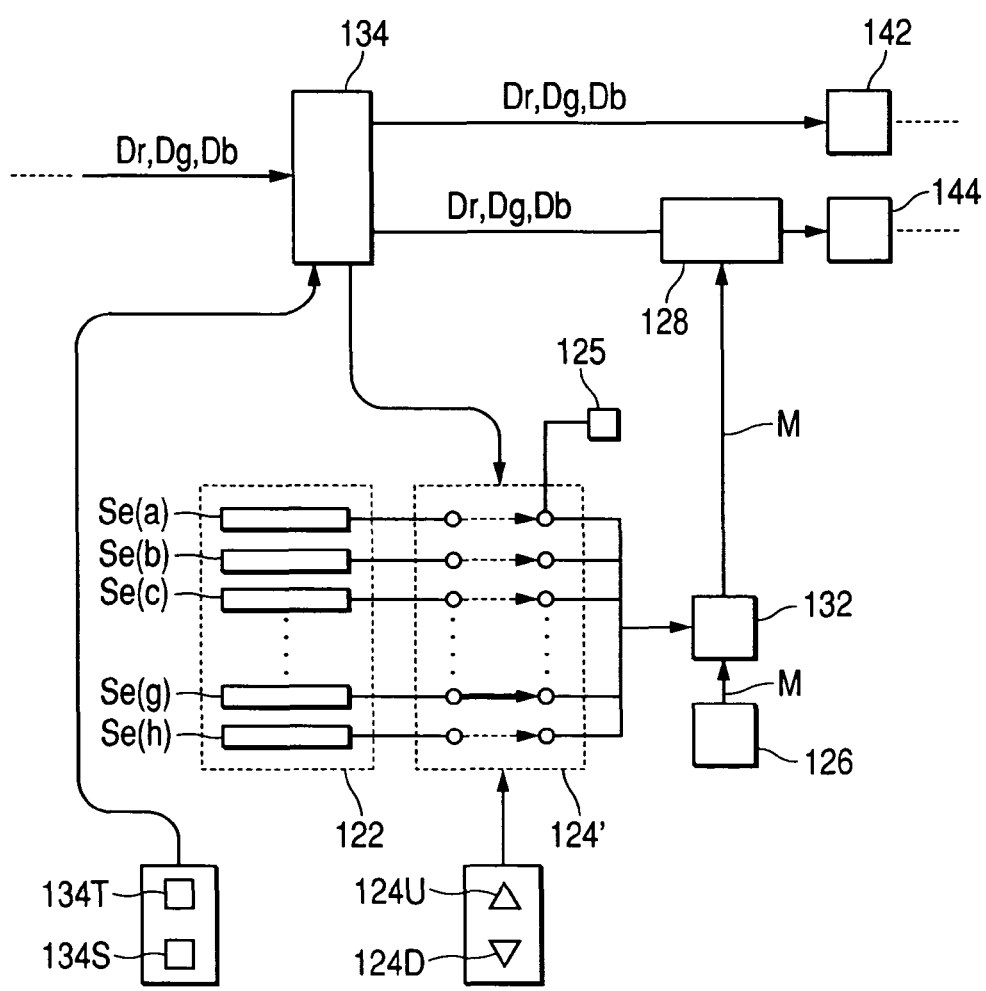
FIG. 11 is an enlarged block diagram showing a schematic configuration of a first modified embodiment.

FIG. 11 is a block diagram showing a schematic configuration of a first modified embodiment, and is an enlarged view of a modification added to a part of FIG. 9.

In the first modified embodiment, the latest wavelength set storing section 136 and the initial display setting section 138 shown in FIG. 9 are omitted, and a wavelength set selecting section 124', which inhibits changing the selecting state of the wavelength set except the case in which the forward switching button 124U or the reverse switching button 124D is operated in the diagnostic image display mode, instead of the wavelength set selecting section 124 described above. Thus, the same operation as the case with the latest wavelength set storing section 136 and the initial display setting section 138 can be realized by this wavelength set selecting section 124'.

Namely, the wavelength set selecting section 124' can memorize the latest wavelength set by detecting a signal from the display mode switching section 134 denoting that the display mode is switched from the diagnostic image display mode to the ordinary image display mode and keeping the state of selecting the latest wavelength set. And, when the display of the image is switched from the ordinary image to the diagnostic image, the latest wavelength set is selected as an initial value of the wavelength set to be selected, and the diagnostic image corresponding to the latest wavelength set can be displayed because the state of selecting the latest wavelength set is kept. Note that the wavelength set selecting section 124' cancels the inhibition of changing the state of the wavelength set selection in response to detection of a signal from the display mode switching section 134 denoting that the image display is switched from the ordinary image to the diagnostic image.

In the case described above, the wavelength set selecting section 124' serves both as the latest wavelength set storing section 136 and the initial display setting section 38 explained with reference to FIG. 9. Other components and operations are the same as those explained with reference to FIG. 9.

Note that the wavelength set selecting section 124' can be equipped with a backup power supply 125, which is a backup section for making it possible to keep the storage of the latest wavelength set even when the drive power of the electronic endoscope apparatus 100 is in the OFF state.

Second Modified Embodiment

Figure 12:
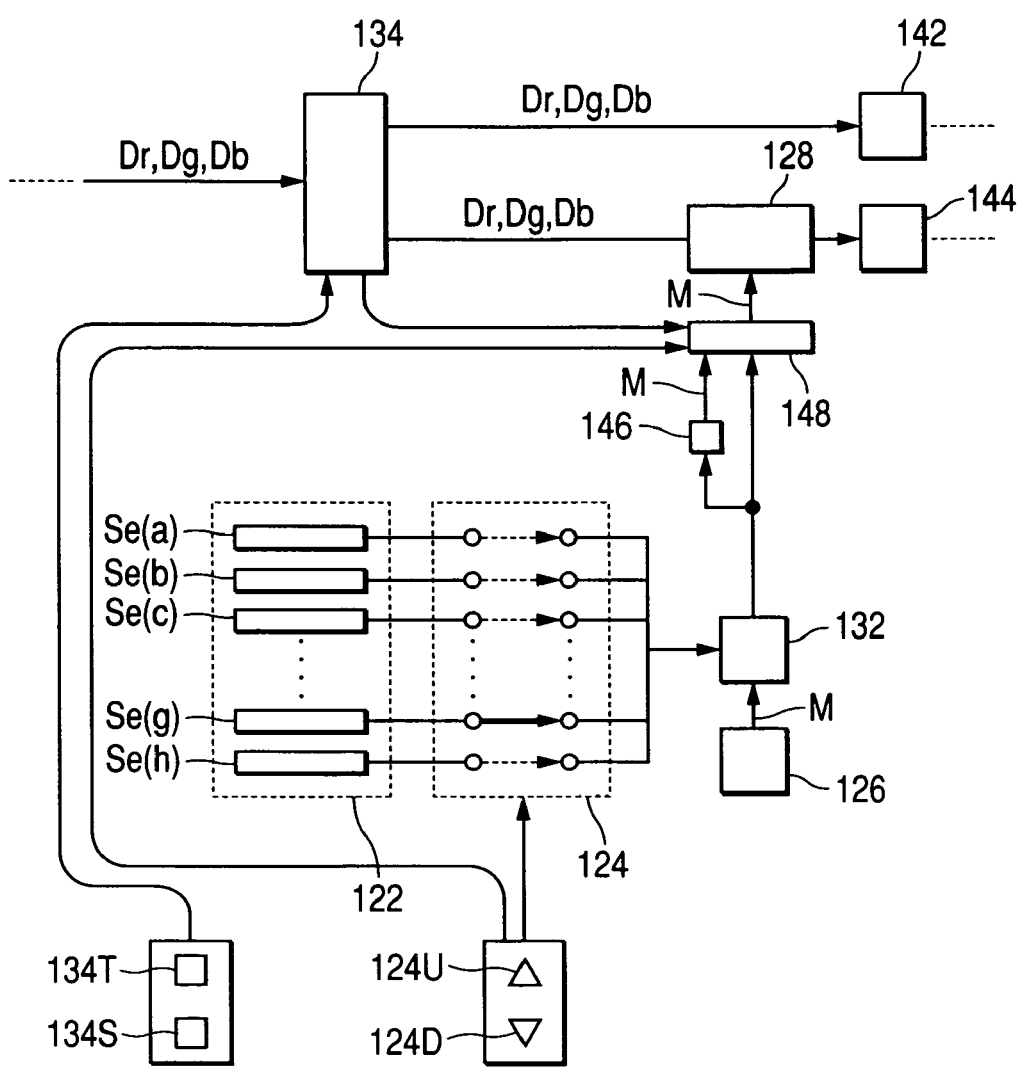
FIG. 12 is an enlarged block diagram showing a schematic configuration of a second modified embodiment.

FIG. 12 is a diagram showing a schematic configuration of a second modified embodiment, and is an enlarged view of a modification added to a part of FIG. 9.

In the second modified embodiment, the latest wavelength set storing section 136 and initial display setting section 138 shown in FIG. 9 are omitted, and a storing section 146 and a transfer control section 148 are provided.

The storing section 146 stores the spectral reflection estimation matrix data M transferred most recently form the matrix data extracting section 132 to the spectral image estimation calculating section 128. Further, the transfer control section 148, in response to detection of mode switching from the ordinary image display mode to the diagnostic image display mode, blocks the transfer of the spectral reflection estimation matrix data from the matrix data extracting section 132 to the spectral image estimation calculating section 128, and transfers the latest spectral reflection estimation matrix data M stored in the string section 146 from the storing section 146 to the spectral image estimation calculating section 128.

Meanwhile, when the transfer control section 148 detects that either of the forward switching button 124U and the reverse switching button 124D is operated in the diagnostic image display mode, the transfer control section 148, in response to the detection, releases the blocked transfer of the spectral reflection estimation matrix data M from the matrix data extracting section 132 to the spectral image estimation calculating section 128.

By providing the storing section 146 and the transfer control section 148, similarly to the first modified embodiment described above, it becomes possible that the most recently selected wavelength set is stored and the diagnostic image corresponding to the latest wavelength set is displayed in response to the image display changed from the ordinary image to the diagnostic image. Other components and operations are the same as those explained with reference to FIG. 9.

Note that, although the storing section 146 stores the spectral reflection estimation matrix data, which has a correspondence with the wavelength set, the storing section 146 can be regarded as substantially storing the latest wavelength set. Therefore, the configuration of the second modified embodiment can be included in the scope of the invention.

The entire disclosure of each and every foreign patent application from which the benefit of foreign priority has been claimed in the present application is incorporated herein by reference, as if fully set forth.

What is claimed is:

1. An endoscope apparatus, comprising:
an endoscope comprising an imaging device that forms color image signals of a body to be observed;
a storage portion that stores matrix data regarding a wavelength range in which a spectral image is constituted;
a spectral image forming circuit that conducts matrix calculation based on the color image signals by using the matrix data of the storage portion to form a spectral image of a selected wavelength range; and
a wavelength selecting section that selects the wavelength range of the spectral image formed by the spectral image forming circuit.

2. The endoscope apparatus according to claim 1, further comprising
a wavelength storing section that stores the wavelength range selected by the wavelength selecting section.

3. The endoscope apparatus according to claim 2,
wherein the wavelength storing section further comprises, in addition to an area that stores the wavelength range, a default data storing area that stores an initial setting value for the wavelength range to be selected by the wavelength selecting section.

4. The endoscope apparatus according to claim 2,
wherein the wavelength storing section further comprises, in addition to the area that stores the wavelength range, a changed wavelength storing area that stores a wavelength range changed after read out from the area that stores the wavelength range.

5. The endoscope apparatus according to claim 4, further comprising
a configuration of storing the changed wavelength range stored in the changed wavelength storing area to the area that stores the wavelength range.

6. The endoscope apparatus according to claim 1, further comprising:
a selector for selecting formation of an ordinary image or that of a spectral image, wherein
the spectral image forming circuit is connected to one output terminal of the selector and a color signal processing circuit for forming the ordinary image is connected to the other output terminal of the selector.

7. The endoscope apparatus according to claim 1,
wherein the wavelength selecting section selects the wavelength range of the spectral image through a continuous changeover.

8. The endoscope apparatus according to claim 1,
wherein the wavelength selecting section selects the wavelength range of the spectral image through a step-wise changeover.

9. The endoscope apparatus according to claim 8, further comprising
a wavelength changeover width setting section that variably sets a changeover width of the wavelength range to be selected by the wavelength selecting section.

10. An endoscope apparatus comprising:
an endoscope comprising an imaging device that forms a color image signals of a body to be observed;
a storage portion that stores matrix data regarding a set of wavelength ranges in which a spectral image is constituted;
a spectral image forming circuit that conducts matrix calculation based on the color image signals by using the matrix data of the storage portion to form a spectral image of a selected set of wavelength ranges; and
a wavelength selecting section that sets a plurality of sets of wavelength ranges, each of the sets of wavelength ranges being for the spectral image formed by the spectral image forming circuit, and selects one of the sets of wavelength ranges by changing the sets of wavelength ranges.

11. The endoscope apparatus according to claim 10,
wherein the wavelength selecting section is able to select a set of wavelength ranges having the same range for formation of a spectral image by a single color mode, from the sets of wavelength ranges.

12. The endoscope apparatus according to claim 10,
wherein the sets of wavelength ranges which can be selected by the wavelength selecting section comprise:
a wavelength set for visualizing a difference between oxyhemoglobin and deoxyhemoglobin;
a wavelength set for visualizing a difference between blood and carotene; and
a wavelength set for visualizing a difference between blood and cytoplasm.

13. The endoscope apparatus according to claim 10, further comprising
a wavelength storing section that stores the set of wavelength ranges selected by the wavelength selecting section.

14. The endoscope apparatus according to claim 13,
wherein the wavelength storing section further comprises, in addition to an area that stores the set of wavelength ranges, a default data storing area that stores a set of initial setting values for the set of wavelength ranges to be selected by the wavelength selecting section.

15. The endoscope apparatus according to claim 13,
wherein the wavelength storing section further comprises, in addition to the area that stores the set of wavelength ranges, a changed wavelength storing area that stores a wavelength range changed after read out from the area for storing the set of wavelength ranges.

16. The endoscope apparatus according to claim 15, further comprising
a configuration of storing the changed wavelength range stored in the changed wavelength storing area to the area that stores the set of wavelength ranges.

17. An electronic endoscope apparatus according to claim 10, which is capable of displaying alternatively by switching an ordinary image of a biological mucous membrane and a diagnostic image of the biological mucous membrane, the diagnostic image being obtained by matrix calculation based on the selected one of said plurality sets of wavelength ranges, the electronic endoscope apparatus comprising
a latest wavelength set storing section that stores the most recently selected one of the sets of wavelength ranges as a latest wavelength set,
wherein the diagnostic image corresponding to the latest wavelength set stored in the latest wavelength set storing section is displayed in response to switching from the ordinary image to the diagnostic image.

18. The electronic endoscope apparatus according to claim 17,
wherein the latest wavelength set storing section comprises a backup section that enables the latest wavelength set storing section to keep storing the latest wavelength set even when a drive power of the electronic endoscope apparatus is in an OFF state.

* * * * *